United States Patent [19]

Bachas et al.

[11] Patent Number: 5,985,117
[45] Date of Patent: Nov. 16, 1999

[54] ION-SELECTIVE MEMBRANE SENSORS WITH MERCURACARBORAND IONOPHORE

[75] Inventors: Leonidas G. Bachas, Lexington, Ky.; M. Frederick Hawthorne, Encino, Calif.; Ibrahim H. A. Badr, Lexington, Ky.

[73] Assignee: The Regents of the University of California, Oakland, Calif.

[21] Appl. No.: 08/999,224

[22] Filed: Dec. 29, 1997

[51] Int. Cl.$^6$ .............................. G01N 27/26; C08F 8/00
[52] U.S. Cl. .............................. 204/418; 525/55; 525/56; 525/57; 525/58; 525/61; 525/165; 524/186; 204/413; 204/415; 204/416
[58] Field of Search .................. 525/55, 56, 57, 525/58, 61, 165; 524/186; 204/413, 415, 416, 418

[56] References Cited

U.S. PATENT DOCUMENTS

| | | | |
|---|---|---|---|
| 4,995,960 | 2/1991 | Wiles et al. | 204/418 |
| 5,174,872 | 12/1992 | Scott | 204/153.1 |
| 5,228,973 | 7/1993 | Sekiguchi et al. | 204/416 |
| 5,464,511 | 11/1995 | Vlasov et al. | 204/153.1 |
| 5,472,590 | 12/1995 | Yamashita et al. | 204/418 |
| 5,531,870 | 7/1996 | Cha | 205/778 |
| 5,554,339 | 9/1996 | Cozzette et al. | 422/50 |
| 5,607,567 | 3/1997 | Yun et al. | 204/418 |

OTHER PUBLICATIONS

Yang, X., Knober, C.B., Hawthorne, M.F., "[12]Mercuracarborand–4", the First Representative of a New Class of Rigid Macrocylic Electrophiles: The Chloride Ion Complex of a Charge–Reversed Analogue of [12]Crown–4, Angewandte Chemie Int. Ed. in Engl., vol. 30, No. 11 (1991), pp. 1507–1508.

Yang, X., Johnson, S.E., Khan, S.I., Hawthorne, M.F., "Multidentate Macrocylic Lewis Acids: Release of '[12] Mercuracarborand–4' from Its Iodide Complex and the Structure of Its Tetra(tetrahydrofuran) Dihydrate Complex," Angewandte Chemie Int. Ed. in Engl., vol. 31, No. 7 (1992), pp. 893–896.

Yang, X.., Knobler, C.B., Hawthorne, M.F., "Macrocyclic Lewis Acid Host–Halide Ion Guest Species. Complexes of Iodide Ion," *J. Am. Chem. Soc.*, 1992, 114, pp. 381–382.

Yang, X., Zheng, Z., Knobler, C.B., Hawthorne, M.F., 'Anti–Crown' Chemistry: Synthesis of [9]Mercuracarborand–3 and the Crystal Structure of Its Acetonitrile Complexes, *J. Am. Chem. Soc.*, 1993, 115, pp. 193–195.

Hawthorne, M.F., Yang, X., Zheng, Z., "Host–guest chemistry of anion–complexation by macrocyclic multidente Lewis acids," *Pure & Appl. Chem.*, vol. 66, No. 2, pp. 245–254, 1994.

Zheng, Z., Yang, X., Knobler, C.B., Hawthorne, M.F., "An Iodide Ion Complex of a Hydrophobic Tetraphenyl [12] Mercuracarborand–4 Having a Sterically Encumbered Cavity," *J. Am. Chem. Soc.*, 1993, 115, pp. 5320–5321.

Yang, X., Knobler, C.B., Hawthorne, M.F., "Supramolecular Chemistry: Molecular Aggregates of Closo–$B_{10}H_{10}^{2-}$ with [12]Mercuracarborand–4," *J. Am. Chem. Soc.*, 1993, 115, pp. 4904–4905.

Hawthorne, M.F., "Host–Guest Chemistry of Anion Complexation by Macrocyclic Multidentate Lewis Acids," *Curr. Top. in the Chem. of Boron*, G.W. Kabalka, ed.; Royal Soc. of Chem., Cambridge, 1994, pp. 207–217.

(List continued on next page.)

*Primary Examiner*—Samuel A. Acquah
*Attorney, Agent, or Firm*—Oppenheimer Wolff & Donnelly LLP

[57] ABSTRACT

Ion-selective membranes are disclosed which are suitable for use in ion-selective sensors. The membranes include a mercuracarborand ionophore. Exemplary ion-selective membranes include Mercuracarborand-3 as the ionophore which is incorporated within a polymer matrix. The ion-selective membranes may be used in a wide variety of ion sensors including ion-selective membrane electrodes.

35 Claims, 6 Drawing Sheets

OTHER PUBLICATIONS

Zheng, Z., Diaz, M., Knobler, C.B., Hawthorne, M.F., "A Mercuracarborand Characterized by B—Hg—B Bonds:Synthesis and Structure of cyclo-[(r-BuMe$_2$Si)$_2$C$_2$B$_{10}$H$_8$Hg]$_3$,"*J. Am. Chem. Soc.*, 1995, 117, pp. 12338–12339.

Zheng, Z., Knobler, C.B., Curtis, C.E., Hawthorne, M.F., "Structure and Bonding of a Novel Mercuracycle Complex Containing B—Hg Bonds at Carborane Vertices," *J. Am. Chem. Soc.*, 1995, 34, pp. 432–435.

Yang, X., Knobler, C.B., Zheng Z., Hawthorne, M.F., "Host–Guest Chemistry of a New Class of Macrocyclic Multidentate Lewis Acids Comprised of Carborane–Supported Electrophile Mercury Centers," *J. Am. Chem. Soc.*, 1994, 116, 7142–7159.

Yang, X., Zheng, Z., Knobler, C.B., Frederick, M.F., "Anti–Crown' Chemistry: Synthesis of [9]Mercuracarborand–3 and the Crystal Structure of Its Acetonitrile Complexes," *J. Am. Chem. Soc.*, 1993, 115, pp. 193–195.

Zheng, Z., Knobler, C.B., Hawthorne, M.F., "Stereoselective Anion Template Effects: Syntheses and Molecular Structures of Tetraphenyl [12]Mercuracarborand–4 Complexes of Halide Ions," *J. Am. Chem. Soc.*, 1995, 117, 5105–5113.

Zheng, Z., Knobler, C.B., Mortimer, M.D., Kong, G., Hawthorne, M.F., "Hydrocarbon–Soluble Mercuracarborands: Syntheses, Halide Complexes, and Supramolecular Chemistry," *Inorg. Chem.*, 1996, 35, pp. 1235–1243.

Zinn, A.A., Zheng, Z., Knobler, C.B., Hawthorne, M.F., "A Hexamethyl Derivative of [9]Mercuracarborand–3: Synthesis, Characterization, and Host–Guest Chemistry," *J. Am. Chem. Soc.*, 1996, 118, pp. 70–74.

Fig. 5 fig. 6 ions utilizing ion-selective electrodes. More particularly, the present invention involves the discovery of a new group of ionophores which may be used in the ion-selective membranes that form an essential component of any ion-selective electrode.

ION-SELECTIVE MEMBRANE SENSORS WITH MERCURACARBORAND IONOPHORE

This invention was made with Government support under Grant No. 9314037, awarded by NSF. The Government has certain rights in this invention.

BACKGROUND OF THE INVENTION

1. Field of the Invention

The present invention relates generally to the detection of ions utilizing ion-selective electrodes. More particularly, the present invention involves the discovery of a new group of ionophores which may be used in the ion-selective membranes that form an essential component of any ion-selective electrode.

2. Description of Related Art

Ion-selective electrodes are widely used in analytical chemistry to measure the concentration of specific ionic substances in fluids. Ion-selective electrodes have been used in a variety of potentiometric ion determinations in fluids ranging from drinking water to biological fluids, such as whole blood, plasma, serum and urine. Typical ions which have been measured using ion-selective electrodes include sodium, calcium, iodide, magnesium, potassium, chloride, and lithium. Generally, ion-selective electrodes are composed of an ion-selective membrane, an internal filling solution or electrolyte and a reference electrode. The ion-selective membrane is an essential element of every ion-selective electrode. Ion-selective membranes are typically formed from a plasticized polymer matrix in which an ionophore selective for the ion or ions of interest is dispersed. U.S. Pat. Nos. 4,995,960, 5,607,567 and 5,531,870 disclose exemplary ion-selective electrodes which utilize polymer matrix membranes which include a variety of different ionophores. Although numerous ionophores have been developed and are presently in use, there is a continuing need to find and develop new ionophores which have desirable ion selectivity when incorporated in a suitable membrane.

Mercuracarborands are a group of compounds which were discovered in the early 1990s and have been investigated for use as possible catalysts. This new class of macrocyclic multidentate Lewis acids are described in detail in the following references: Zheng et al., "Stnicture and Bonding of a Novel Mercuracycle Complex Containing B—Hg Bonds at Carboranc Vertices," *Inorgainic Chemistry*, Vol. 34, No. 2, 1995, 432–435; Yang et al., "Host-Guest Chemistry of a New Class of Macrocyclic Multidentatc Lewis Acids Comprised of Carboranc-Supported Electrophilic Mercury Centers," *J Am. Chem.* Soc. 1994, 116, 7142–7159; Yang et al., "'Anti-Crown' Chemistry: Synthesis of [9]Mercuracarborand-3 and the Crystal Structure of Its Acetonitrile Complexes," *J Am. Chem. Soc.*, Vol. 115, No. 1, 1993, 193–195; Zheng et al., "Stereoselective Anion Template Effects: Syntheses and Molecular Structures of Tetraphenyl [12]Mercuracarborand-4 Complexes of Halide Ions, *J Am. Chem. Soc.*, Vol. 117, 1995, 5105–5113; Zheng et al., "Hydrocarbon-Soluble Mercuracarborands: Syntheses, Halide Complexes, and Supramolecular Chemistry," *Inorganic Chemistry*, Vol 35, 1996, 1235–1243; Zinn et al., "A Hexamethyl Derivative of [9]Mercuracarborand-3: Synthesis, Characterization, and Host-Guest Chemistry," *J Am. Chem. Soc.*, Vol. 118, 1996, 70–74. Although mercuracarborand compounds have been synthesized and studied extensively, there has been no investigation of their possible use as ionophores in ion-selective membranes.

The above-cited articles, as well as all of the other patents and references referred to in this specification, are hereby incorporated by reference.

SUMMARY OF THE INVENTION

In accordance with the present invention, it was discovered that [9]Mercuracarborand-3 may be used as an ionophore in ion-selective electrodes. [9]Mercuracarborand-3 and other related mercuracarborand compounds are useful as ionophores in a wide variety of ion-selective electrodes. [9]Mercuracarborand-3 is especially well-suited for use in a plasticized polymer matrix membrane for conducting potentiometric determinations of chloride ion concentrations in fluids. Mercuracarborand compounds, including [9]Mercuracarborand-3, are particularly well-suited for use as ionophorcs in ion-selective membranes, and the corresponding ion-selective electrodes exhibit very good selectivity and sensitivity. In addition, they exhibit fast response times, fast recovery times, and relatively long lifetimes. Such attributes are especially desirable for potentiometric determinations including clinical and environmental analyses.

The above discussed and many other features and attendant advantages of the present invention will become better understood when considered in conjunction with the accompanying drawings.

DETAILED DESCRIPTION OF THE INVENTION

The present invention is based on the discovery that [9]Mercuracarborand-3 and related mercuracarborand compounds can be used as an ionophore in ion-selective membranes which in turn form a critical element of ion-selective electrodes. [9]Mercuracarborand-3 was first isolated in the early 1990s by Professor M. Frederick Hawthorne and his research group at the University of California in Los Angeles. The references listed in the background of the invention provide details of the preparation and isolation of [9]Mercuracarborand-3, the structure of which is shown in FIG. 2[A] (x=H). [9]Mercuracarborand-3 can be made from readily available starting materials as set forth in the referenced articles which have been incorporated by reference herein.

Figure 2:
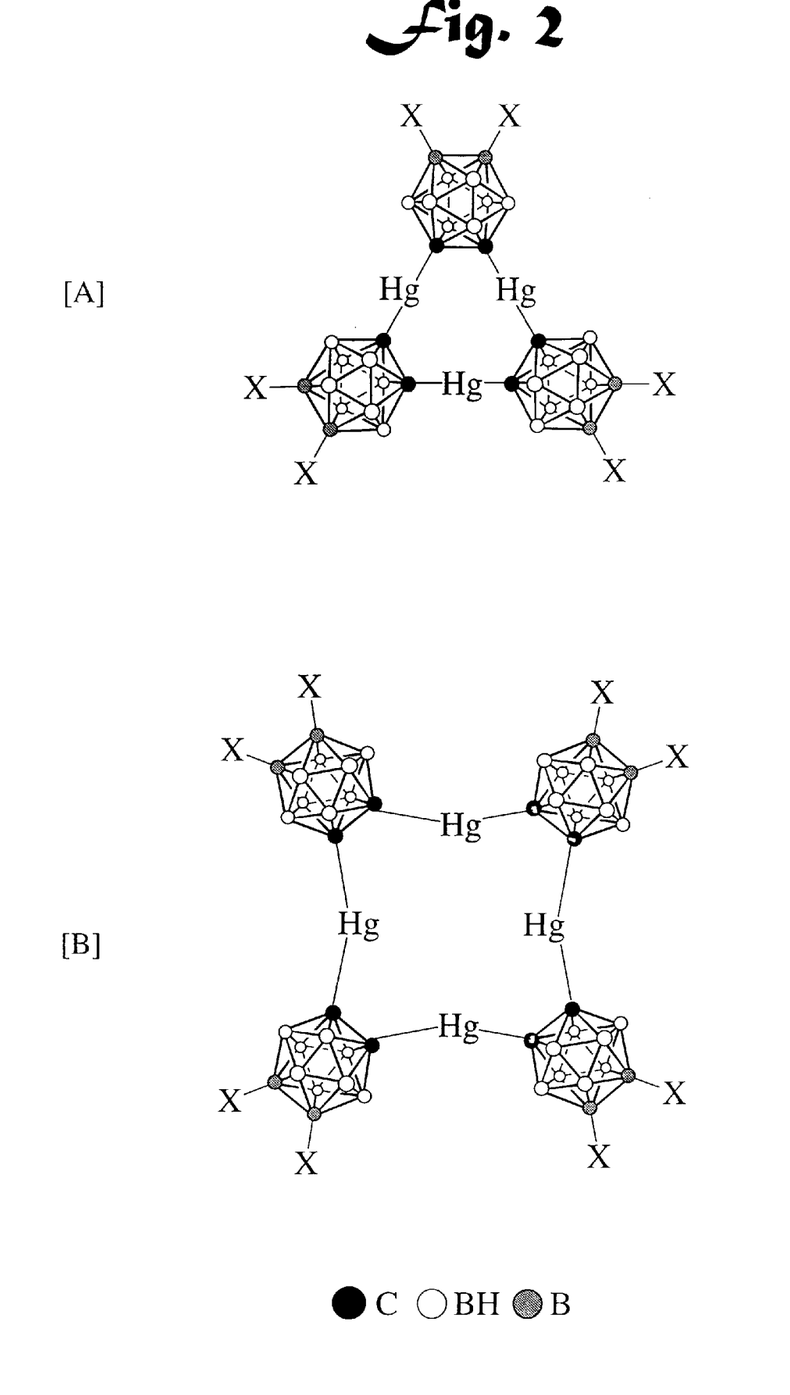
FIG. 2 shows structural drawings of [9]Mercuracarborand-3 (FIG. 2A); x=H and related mercuracarborand compounds (FIGS. 2A and 2B) in accordance with the present invention.

Examples of compounds related to [9]Mercuracarborand-3 which are also suitable for use as ionophores are also shown in FIG. 2. In general, these compounds differ in terms of the size of the mercuracarborand macrocycle and the position and nature of the substituents. Although the substituents in FIG. 2 are drawn at positions 9 and 12 of the carborane ligand, compounds with one or more substituents at different positions are also potential ionophores. Examples of the substituents X include H, $CH_3$, $CH_2CH_3$, $(CH_2)_5CH_3$, $C(C_6H_5)_3$, $C(CH_3)_3$, $C(CH_2CH_3)_3$, $C_6H_5$, $C_6F_5$, I, F, etc. The structural formulas for the above-listed compounds are set forth in FIG. 2A and 2B. The above group of compounds and any additional mercuracarborand compounds which may function as an ionophore are referred to herein as mercuracarborand ionophores.

Exemplary synthesis protocols for the above-listed mercuracarborand ionophores are as follows:

The general synthesis of [9]mercuracarborand-3 which is set forth below is described in detail in Yang, X., Zheng, Z., Knobler, C., Hawthorne, M. F., *J Am. Chem. Soc.* 1993, vol. 115, 193–195; and Zinn, A. A., Zheng, Z., Knobler, C. B., Hawthorne, M. F., *J Am. Chem. Soc.* 1996, vol. 118, 70–74.

A solution of butyllithium is added to an ethereal solution of ortho-carborane at 0° C., and the slurry that forms is stirred at room temperature under argon atmosphere. After four hours the mixture is brought back to 0° C. and treated with solid mercuric acetate. The stirring is continued overnight, while the mixture warms to room temperature. The mixture is then treated with distilled water, and the organic phase is washed three times with water and dried over magnesium sulfate. The solvent is removed and the residue is recrystallized from ether.

Although mercuracarborand ionophores can be incorporated into a wide variety of ion-selective membrane materials, it is preferred that membranes composed of polymer matrices be utilized. In addition, in accordance with conventional procedures, it is preferred that the polymer matrices be plasticized and include one or more membrane additives (also referred to as ionic additives). The preparation of a wide variety of plasticized polymer membranes are well-known and are suitable candidates for use in connection with the mercuracarborand ionophore in accordance with the present invention. Exemplary polymers which can be used to form a polymer membrane include poly(vinyl chloride), poly(vinyl chloride) carboxylated, cellulose triacetate, silicon rubber, polyurethane and copolymers of vinyl chloride, vinyl acetate and vinyl alcohol. Exemplary plasticizers include bis(1-butylpentyl) adipate, bis(2-ethylhexyl) adipate, bis(2-ethylhexyl) phthalate, bis(2-ethylhexyl) sebacate and o-nitrophenyloctyl ether. Exemplary ionic additives include tridodecylmethylammonium chloride (TDMAC) and tetradecylmethyl-ammonium chloride. The various procedures for incorporation of the plasticizer, ionophore and ionic additive, are well-known in the ion-selective electrode art. In general, [9]Mercuracarborand-3 and other mercuracarborand ionophores may be substituted for other ionophores in situations where good selectivity and sensitivity is required. The mercuracarborand ionophores are also useful where fast response and recovery times are needed as well as long membrane lifetimes.

A preferred ion-selective membrane in accordance with the present invention includes [9]Mercuracarborand-3 as the ionophore, o-nitrophenyloctyl ether as the plasticizer, poly (vinyl chloride) as the polymer matrix, and tridodecylmethyl-ammonium chloride as the ionic additive. The relative amounts of these ingredients in the membrane may be varied within conventional standards. For example, the amount of [9]Mercuracarborand-3 can be varied from 0.5 to 5 weight percent. The amount of plasticizer may be varied from about 0 to 70 weight percent, and the amount of ionic additive may be varied from 0 to 100 mole percent (relative to the amount of the ionophore). The above-described preferred electrode is especially useful for conducting potentiometric determinations for chloride ion. Other exemplary membranes include: (1) 33 weight percent cellulose triacetate, 1 weight percent [9]Mercuracarborand-3, 66 weight percent o-nitrophenyloctyl ether and 10 mole percent (relative to the amount of the ionophore) TDMAC; (2) 60 weight percent polyurethane, 1 weight percent [9]Mercuracarborand-3, 39 weight percent o-nitrophenyloctyl ether and 5 mole percent (relative to the amount of the ionophore) TDMAC.

Figure 1:
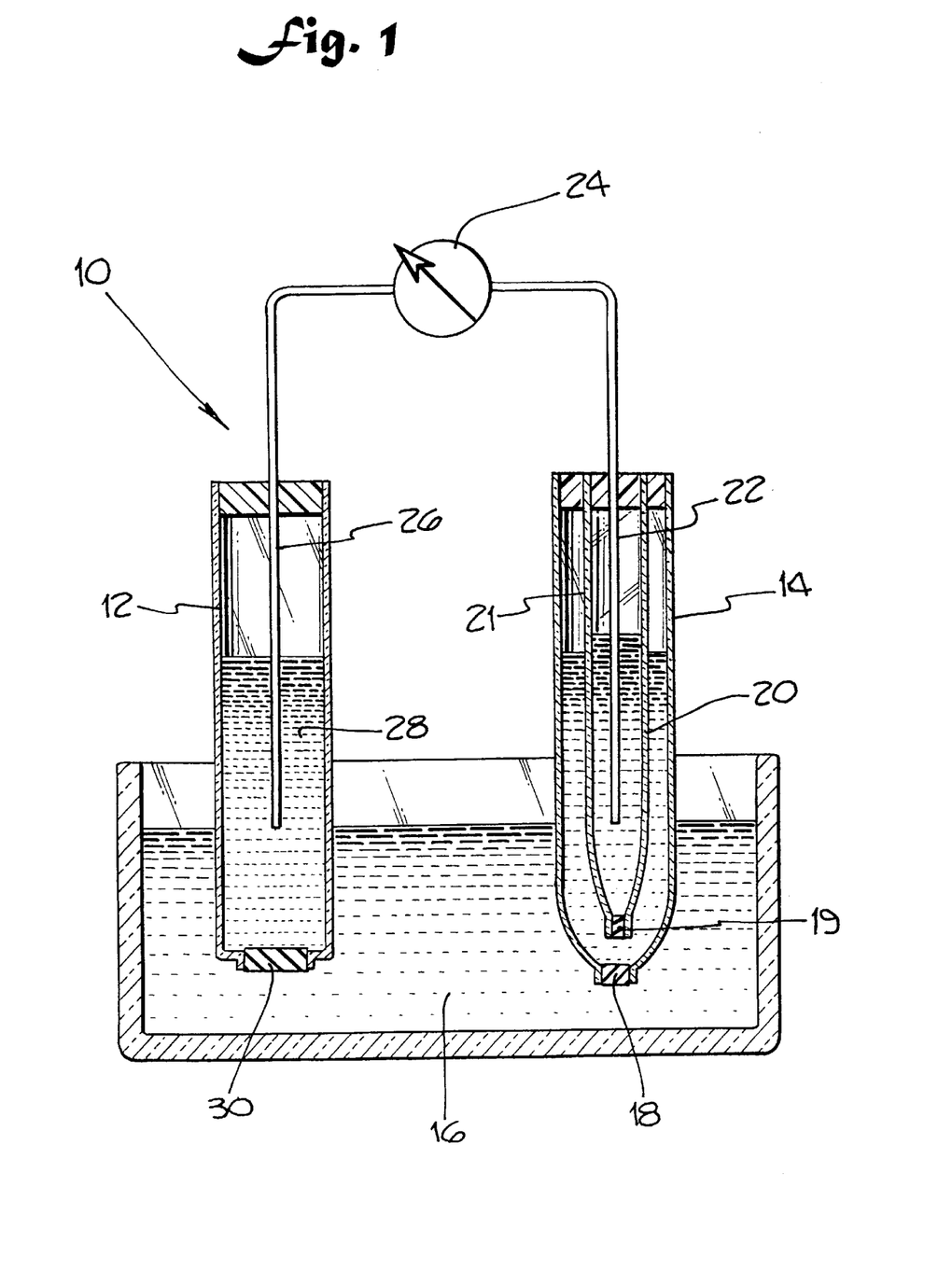
FIG. 1 is an exemplary system for conducting ion-selective potentiometric determinations utilizing the ion-selective membrane in accordance with the present invention.

A schematic diagram of a potentiometric cell assembly for measuring ion concentrations in a fluid employing the ion-selective electrode of the present invention is shown generally at 10 in FIG. 1. The assembly is conventional in nature in that it includes an ion-selective electrode 12 and external reference electrode 14 (double junction reference electrode). The electrode assembly is shown immersed in solution 16 in which ions of interest are to be measured. The reference electrode includes liquid junctions 18 and 19, double-junction filling solution 20, internal filling solution 21, as well as a conventional silver/silver chloride wire 22. The electrodes 12 and 14 are connected to a potentiometer 24 or other device for measuring the electromotive force (EMF) generated between the electrodes 12 and 14 during immersion in solution 16.

The ion-selective electrode includes a silver/silver chloride wire 26, as well as an internal filling solution 28. The ion-selective membrane in accordance with the present invention is shown at 30. The internal filling solutions 21 and 28 used in the reference and ion-selective electrodes, respectively, and the double-junction filling solution 20 can be any of those solutions used in conventional ion-selective electrode systems. For example, the internal filling solution 21 for the reference electrode may be potassium chloride. The double-junction filling solution 21 for the reference electrode may be potassium nitrate or lithium acetate. The internal filling solutions 21 and 28 for the reference and ion-selective electrode may be 0.01M sodium chloride or 0.01M potassium chloride.

The system 10 shown in FIG. 1 can be used to measure the presence of a wide variety of ions in a multitude of different solutions. In addition to measuring chloride ions, the system is useful in measuring other halides, such as bromide or iodide, as well as thiocyanate. The system 10 can be used to measure ions in a wide range of fluids including water, whole blood, serum, plasma, urine, environmental samples such as soil extracts, ground water and industrial effluents.

The system 10 functions in accordance with principles and procedures well established for other ion-selective electrode assemblies, except that a mercuracarborand ionophore in accordance with the present invention, along with a suitable polymer matrix, plasticizer and ionic or membrane additive are utilized.

Examples of practice are as follows:

Electrode membranes 30 which are sensitive for chloride were constructed using [9]Mercuracarborand-3 as the ionophore, o-nitrophenyloctyl ether as the plasticizer, poly (vinyl chloride) as the polymer matrix, and different mole percentages (relative to the ionophore) of tridodecylmethylammonium chloride as the ionic or membrane additive. The membrane was prepared as follows: the membrane components were dissolved in tetrahydrofuran and cast into a glass ring placed on a glass plate. The solvent was then allowed to evaporate.

As set forth in Table 1, membrane electrodes in accordance with the present invention doped with different levels of ionic additives (TDMAC) respond well to chloride ion over a wide linear range with good detection limits.

TABLE 1

| Membrane | TDMAC, mole % | Linear range, M | Detection limit, $\mu M$ | Slope, mV/decade |
|---|---|---|---|---|
| I | 5 | $10^{-5}$–$10^{-2}$ | 3.59 | −53.4 |
| II | 10 | $10^{-5}$–$10^{-2}$ | 5.86 | −53.4 |
| III | 60 | $10^{-5}$–$10^{-2}$ | 7.06 | −56.8 |

Figure 3:
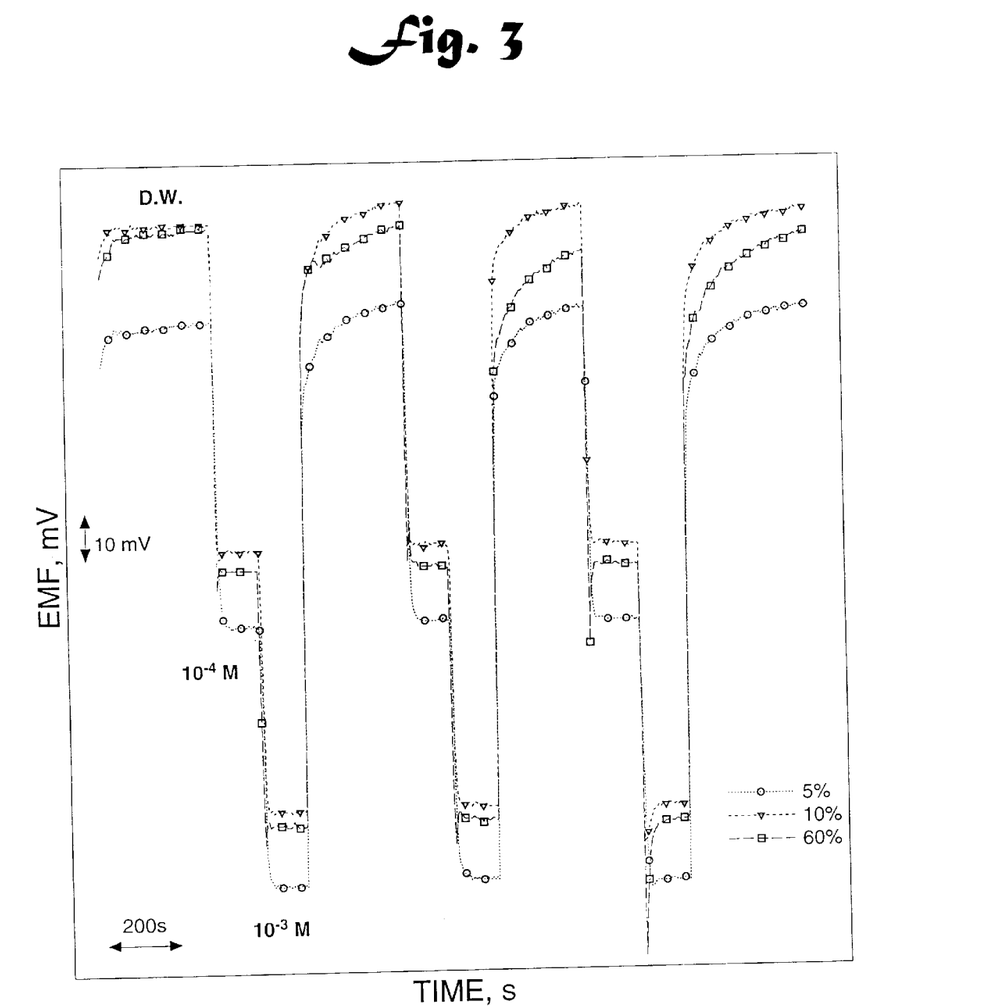
FIG. 3 is a graph showing the response time and reversibility of preferred exemplary chloride sensors in accordance with the present invention.

The chloride-selective membrane electrodes with varying levels of ionic additive were tested for reproducibility, response time, and reversibility to baseline potential. As shown in FIG. 3, the electrodes showed response timeibility, fast response times, and fast reversibility to baseline potential. The equilibrium potential is reached within a few seconds after changing the sample chloride concentration either from 0 (deonized water, D.W.) to $1 \times 10^{-4}$ M or from $1 \times 10^{-4}$ M to $1 \times 10^{-3}$ M. In addition, the recovery of the [9]Mercuracarborand-3 based sensor is achieved in a very short time wherein the sensors reached the baseline potential after exposure to $1 \times 10^{-3}$ M in less than one minute (see Table 2).

TABLE 2

| Membrane | $t_{90\%}$,s $0 \to 10^{-4}$ M | $t_{90\%}$,s $10^{-4}$ M $\to 10^{-3}$ M | Recovery, $t_{90\%}$,s |
|---|---|---|---|
| I | 13.3 | 11.7 | 30.3 |
| II | 8.0 | 8.0 | 24.3 |
| III | 5.0 | 5.6 | 42.7 |

Figure 4:
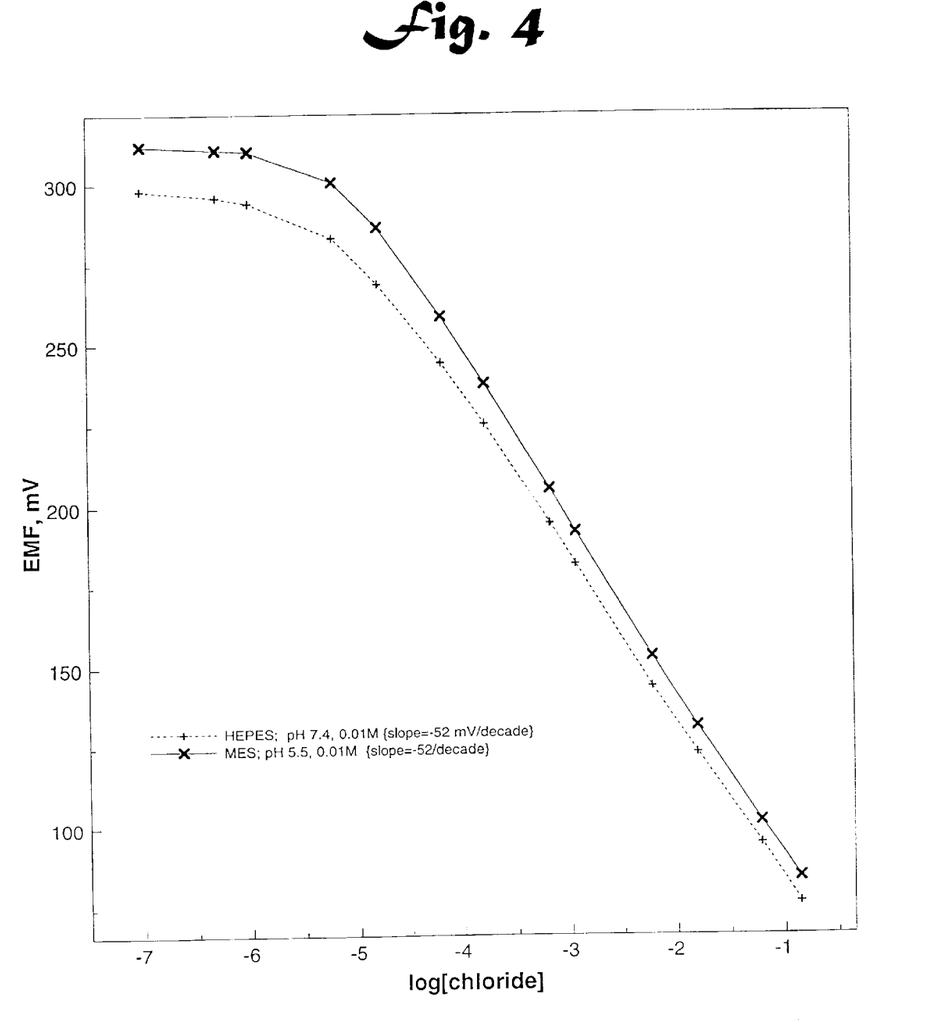
FIG. 4 is another graph showing the chloride response of ion-selective electrodes in accordance with the present invention.

In addition, it was found that chloride-selective membrane electrodes based on [9]Mercuracarborand-3 show practically no pH response over the pH range of 2.5 to 7, which enables the utilization of such sensors in clinical applications without significant loss of either detection limit or slope of the chloride response. As shown in FIG. 4, a [9]Mercuracarborand-3-based electrode (doped with 60 mole % tridodecylmethylammonium chloride gave similar detection limit and slope of the calibration plot toward chloride in 0.01M 2-[N-Morpholino]ethanesulfonic acid (MES) buffer, pH 5.5, and in 0.01M N-[2-hydroxyethyl] piperazine-N'-[2-ethane-sulfonic acid] (HEPES) buffer, pH 7.4.

Figure 5:
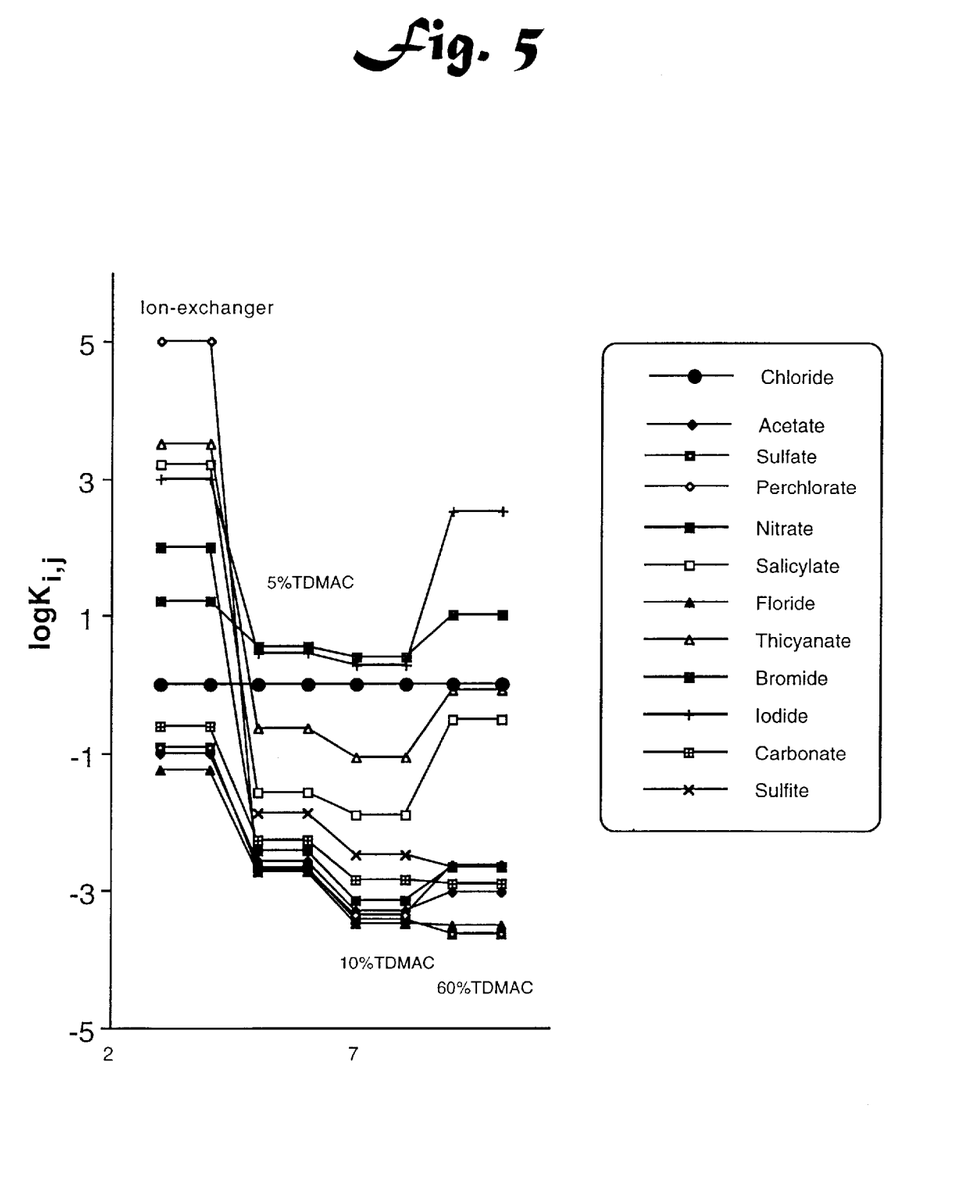
FIG. 5 is a graph showing test results demonstrating the selectivity patterns of chloride sensors in accordance with the present invention.

For analytical applications, the selectivity of a sensor is one of the most important parameters. [9]Mercuracarborand-3-based chloride sensors doped with tridodecylmethylammonium chloride as set forth in Table 1 show a significant enhancement of chloride selectivity in comparison with the ion-exchanger based membranes that are used in conventional ion-exchanger based chloride-selective electrodes (see data in FIG. 5). In addition, the high chloride selectivity over biologically important anions (e.g., carbonate, phosphate, sulfate, salicylate, thiocyanate) obtained using [9]Mercuracarborand-3-based chloride sensors should allow the determination of chloride in biological fluids. As shown in Table 3, the chloride selectivity coefficients obtained are smaller (i.e., selectivity is better) than those required for determination of chloride with <1% error.

TABLE 3

| | 95% normal concentration | | log $K_{Cl,j}^{pot}$ | | |
|---|---|---|---|---|---|
| Anion | range (mmol L$^{-1}$)$^a$ | Required$^b$ | 5 mole % TDMAC | 10 mole % TDMAC | 60 mole % TDMAC |
| chloride | 95–110 | 0.0 | 0.0 | 0.0 | 0.0 |
| bromide | 0.009–0.17 | ≦0.7 | 0.55 | 0.39 | 0.99 |
| thiocyanate | 0.007–0.017 | ≦1.7 | −0.64 | −1.05 | −0.09 |
| | (0.15)$^c$ | (0.8)$^c$ | | | |
| salicylate | 2.2$^d$ | ≦−0.3 | −1.56 | −1.9 | −0.5 |
| bicarbonate | 21.3–26.5 | ≦−1.4 | −2.26 | −2.85 | −2.9 |
| HPO$_4^{2-}$ | 0.26–0.89 | ≦−1.2 | −2.8 | −3.8 | −3.6 |
| sulfate | 0.3–1.0 | ≦−1.3 | −2.7 | −3.4 | −3.6 |

$^a$For whole blood, plasma and serum.
$^b$Calculated for a minimum error of 1% due to the presence of interfering anion.
$^c$For smokers.
$^d$Maximum, therapeutic dosage (in plasma).

Figure 6:
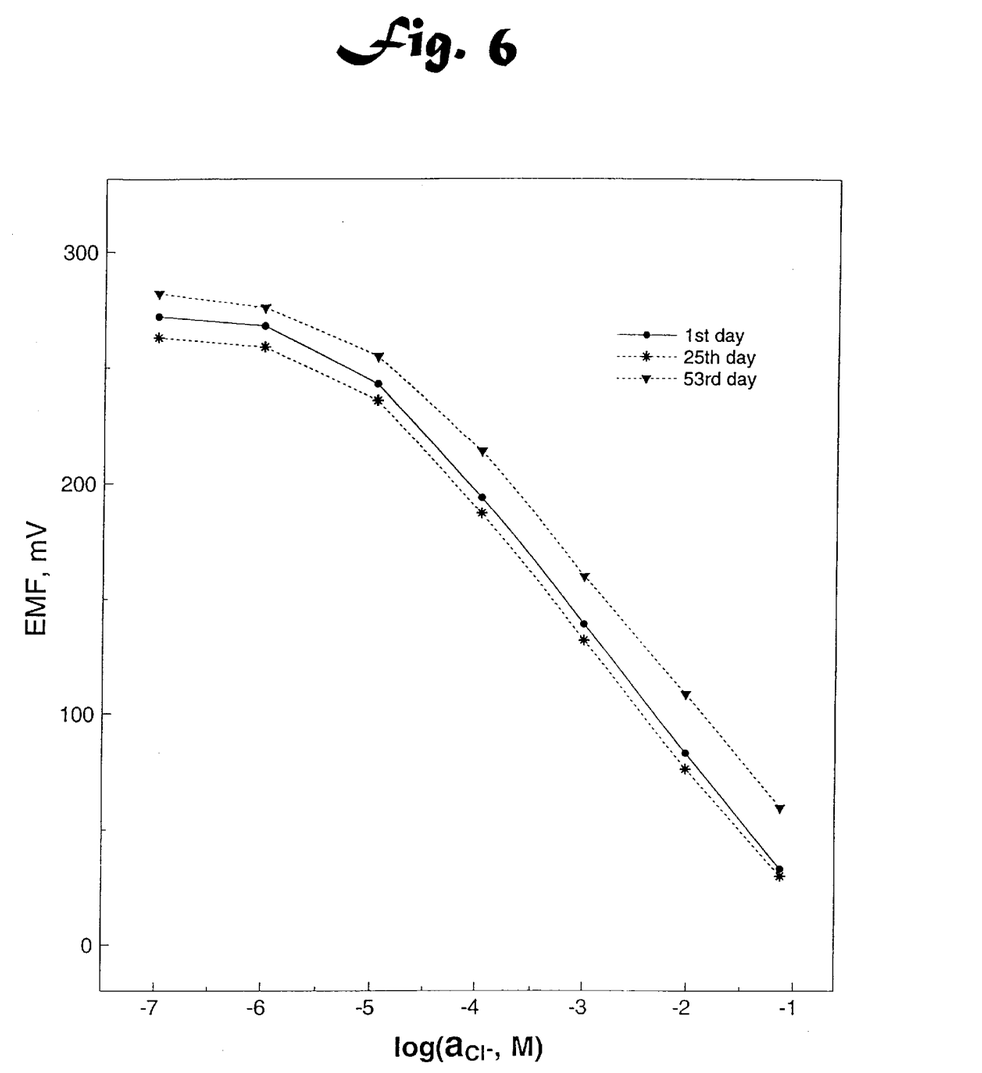
FIG. 6 is a chloride response curve of exemplary ion-selective sensors measured in different time periods in accordance with the present invention.

The lifetime of the sensor membranes in accordance with the present invention was evaluated over a period of 53 days. Data obtained showed that the membranes have a long lifetime, where the sensor's slope and detection limit did not practically change over that time period (see data in FIG. 6 for membrane electrode III). As shown in Table 4, the selectivity for a 53-day old sensor was practically very close to that of the freshly prepared sensor (in brackets).

TABLE 4

| | log $K_{Cl,j}^{pot}$ | | |
|---|---|---|---|
| Membrane | Perchlorate | Nitrate | Thiocyanate |
| II | −2.71 [−2.43] | −2.86 [−2.43] | −0.88 [−0.25] |
| III | −3.05 [−3.16] | −3.02 [−3.13] | −0.87 [−0.73] |
| IV | −2.46 [−2.30] | −2.70 [−2.55] | −0.38 [0.12] |

Additional membrane electrodes can be prepared as in Table 1 but with different plasticizers (e.g., dioctyl sebacate, dioctyl phthalate, etc.), and/or other polymer matrices (e.g., cellulose triacetate, polyurethane, etc.) and/or lipophilic additives.

As is apparent from the above description, ion-selective sensors utilizing mercuracarborand compounds as the ionophore in accordance with the present invention will be useful in determining chloride ions as well as other ions in a wide variety of biological fluids, environmental samples and industrial fluids. Membranes incorporating the ionophore in accordance with the present invention can also be utilized in the development of miniaturized solid state ion sensors.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. An ion-selective membrane adapted for use in an ion-selective electrode, said membrane comprising an ionophore wherein said ionophore is a mercuracarborand ionophore.

2. An ion-selective membrane according to claim 1 wherein said mercuracarborand ionophore is Mercuracarborand-3.

3. An ion-selective membrane according to claim 1 wherein said membrane comprises a polymer matrix.

4. An ion-selective membrane according to claim 3 wherein said ionophore is covalently attached to said polymer matrix.

5. An ion-selective membrane according to claim 3 wherein said polymer matrix comprises a polymer selected from the group consisting of poly(vinyl chloride), poly(vinyl chloride) carboxylated, cellulose triacetate, silicon rubber, polyurethane and copolymers of vinyl chloride, vinyl acetate and vinyl alcohol.

6. An ion-selective membrane according to claim 3 wherein said polymer matrix is plasticized with a plasticizer.

7. An ion-selective membrane according to claim 6 wherein said plasticizer is selected from the group consisting of bis(1-butylpentyl) adipate, bis(2-ethylhexyl) adipate, bis(2-ethylhexyl) phthalate, bis(2-ethylhexyl) sebacate and o-nitrophenyloctyl ether.

8. An ion-selective membrane according to claim 3 wherein said polymer matrix contains an ionic additive.

9. An ion-selective membrane according to claim 8 wherein said ionic additive is selected from the group consisting of tridodecylmethylammonium chloride and tetradecylmethylammonium chloride.

10. An ion-selective membrane according to claim 6 wherein said polymer matrix contains an ionic additive.

11. An ion-selective membrane according to claim 3 wherein said polymer is poly(vinyl chloride).

12. An ion-selective membrane according to claim 7 wherein said plasticizer is o-nitrophenyl octyl ether.

13. An ion-selective membrane according to claim 9 wherein said ionic additive is tridodecylmethylarnmonium chloride.

14. An ion-selective membrane according to claim 11 which further comprises o-nitrophenyl octyl ether as a plasticizer and tridodecylmethylammonium chloride as an ionic additive.

15. An ion-selective electrode which comprises an ion-selective membrane, said membrane comprising an ionophore wherein said ionophore is a mercuracarborand ionophore.

16. An ion-selective electrode according to claim 15 wherein said mercuracarborand ionophore is Mercuracarborand-3.

17. An ion-selective electrode according to claim 15 wherein said ion-selective membrane comprises a polymer matrix in which said ionophorc is dispersed.

18. An ion-selective electrode according to claim 17 wherein said ionophore is covalently attached to said polymer matrix.

19. An ion-selective electrode according to claim 17 wherein said polymer matrix comprises a polymer selected from the group consisting of poly(vinyl chloride), poly(vinyl chloride) carboxylated, cellulose triacetate, silicon rubber, polyurethane and copolymers of vinyl chloride, vinyl acetate and vinyl alcohol.

20. An ion-selective electrode according to claim 17 wherein said polymer matrix comprises a plasticizer.

21. An ion-selective electrode according to claim 20 wherein said plasticizer is selected from the group consisting of bis(1-butylpentyl) adipate, bis(2-ethylhexyl) adipate, bis(2-ethylhexyl) phthalate, bis(2-ethylhexyl) sebacate and o-nitrophenyloctyl ether.

22. An ion-selective electrode according to claim 17 wherein said polymer matrix comprises an ionic additive.

23. An ion-selective electrode according to claim 22 wherein said ionic additive is selected from the group consisting of tridodecylmethylammonium chloride and tetradccylmethylammonium chloride.

24. A method for detecting the presence of ions in a fluid using an ion-selective electrode which comprises an ion-selective membrane, said membrane comprising an ionophore, the improvement comprising using a mercuracarborand ionophore as said ionophore.

25. An improved method according to claim 24 wherein said mercuracarborand ionophore is Mercuracarborand-3.

26. An improved method according to claim 24 wherein said membrane comprises a polymer matrix.

27. An improved method according to claim 24 wherein said mercuracarborand ionophore is covalently attached to said polymer matrix.

28. An improved method according to claim 26 wherein said polymer matrix comprises a plasticizer.

29. An improved method according to claim 28 wherein said polymer matrix comprises an ionic additive.

30. An improved method according to claim 29 wherein said ion being tested for in said fluid is chloride ion.

31. An improved method according to claim 26 wherein said polymer matrix comprises a polymer selected from the group consisting of poly(vinyl chloride), poly(vinyl chloride) carboxylated, cellulose triacetate, silicon rubber, polyurethane and copolymers of vinyl chloride, vinyl acetate and vinyl alcohol.

32. An improved method according to claim 28 wherein said plasticizer is selected from the group consisting of bis(1-butylpentyl) adipate, bis(2-ethylhexyl) adipate, bis(2-ethylhexyl) phthalate, bis(2-ethylhexyl) sebacate and o-nitrophenyl-octyl ether.

33. An improved method according to claim 29 wherein said ionic additive is selected from the group consisting of tridodecylmethylammonium chloride and tetradecylmethylammonium chloride.

34. In an ion-selective electrode which comprises an ion-selective membrane, said membrane comprising an ionophore, the improvement comprising using a mercuracarborand ionophore as said ionophore.

35. A system for measuring ions in fluid, said system comprising:
   an ion-selective electrode according to claim 15;
   a reference electrode; and
   a device for measuring the electromotive force between said ion-selective electrode and said reference electrode.

* * * * *